(12) United States Patent
Knapp et al.

(10) Patent No.: US 7,953,499 B2
(45) Date of Patent: May 31, 2011

(54) DRUG-ELUTING ELECTRODE

(75) Inventors: Christopher P. Knapp, Ham Lake, MN (US); Steve Allex, Shoreview, MN (US); Carolyn Wineland, Chelsea, MI (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 504 days.

(21) Appl. No.: 10/675,920

(22) Filed: Sep. 30, 2003

(65) Prior Publication Data

US 2005/0070985 A1 Mar. 31, 2005

(51) Int. Cl.
*A61N 1/05* (2006.01)
(52) U.S. Cl. .......................... 607/120; 607/121
(58) Field of Classification Search .......... 607/120–121, 607/127, 119, 122
See application file for complete search history.

(56) References Cited

U.S. PATENT DOCUMENTS

| | | | |
|---|---|---|---|
| 4,280,514 A * | 7/1981 | MacGregor | 607/121 |
| 4,281,669 A * | 8/1981 | MacGregor | 607/121 |
| 4,506,680 A * | 3/1985 | Stokes | 607/120 |
| 4,606,118 A | 8/1986 | Cannon et al. | |
| 4,711,251 A | 12/1987 | Stokes | |
| 4,953,564 A * | 9/1990 | Berthelsen | 607/120 |
| 4,972,848 A | 11/1990 | DiDomenico et al. | |
| 5,002,067 A | 3/1991 | Berthelsen et al. | |
| 5,003,992 A | 4/1991 | Holleman et al. | |
| 5,009,229 A | 4/1991 | Grandjean et al. | |
| 5,086,787 A | 2/1992 | Grandjean et al. | |
| 5,103,837 A * | 4/1992 | Weidlich et al. | 607/120 |
| 5,154,183 A | 10/1992 | Kreyenhagen et al. | |
| 5,217,028 A | 6/1993 | Dutcher et al. | |
| 5,255,693 A | 10/1993 | Dutcher et al. | |
| 5,282,844 A | 2/1994 | Stokes et al. | |
| 5,306,292 A * | 4/1994 | Lindegren | 607/11 |
| 5,324,324 A * | 6/1994 | Vachon et al. | 607/120 |
| 5,324,325 A | 6/1994 | Moaddeb | |
| 5,342,628 A | 8/1994 | Picha | |
| 5,345,933 A | 9/1994 | Peterson et al. | |
| 5,411,527 A | 5/1995 | Alt | |
| 5,423,876 A | 6/1995 | Camps et al. | |
| 5,447,533 A | 9/1995 | Vachon et al. | |
| 5,489,294 A | 2/1996 | McVenes et al. | |
| 5,522,874 A | 6/1996 | Gates | |
| 5,522,875 A | 6/1996 | Gates et al. | |
| 5,551,427 A | 9/1996 | Altman | |

(Continued)

FOREIGN PATENT DOCUMENTS

EP 0791372 8/1997

(Continued)

OTHER PUBLICATIONS

"International Search Report for corresponding PTC Application No. PCT/US2004/032064", (Dec. 21, 2004), 3 pgs.

(Continued)

*Primary Examiner* — Michael Kahelin
(74) *Attorney, Agent, or Firm* — Faegre & Benson LLP

(57) ABSTRACT

An apparatus includes an electrical lead comprising a lead body and an electrical conductor, and an electrode coupled to the electrical conductor, wherein the electrode includes a coating on at least a portion of a surface of the electrode, the coating including two or more layers, with a first layer adjacent the surface of the electrode comprising an insulative material and a second layer adjacent the first layer comprising at least one pharmacological agent.

38 Claims, 2 Drawing Sheets

U.S. PATENT DOCUMENTS

| | | | |
|---|---|---|---|
| 5,575,814 A | 11/1996 | Giele et al. | |
| 5,776,178 A | 7/1998 | Pohndorf et al. | |
| 5,964,794 A * | 10/1999 | Bolz et al. | 607/121 |
| 5,987,746 A | 11/1999 | Williams et al. | |
| 6,086,582 A | 7/2000 | Altman et al. | |
| 6,102,887 A | 8/2000 | Altman | |
| 6,231,570 B1 | 5/2001 | Tu et al. | |
| 6,253,110 B1 | 6/2001 | Brabec et al. | |
| 6,256,542 B1 | 7/2001 | Marshall et al. | |
| 6,263,249 B1 | 7/2001 | Stewart et al. | |
| 6,287,285 B1 | 9/2001 | Michal et al. | |
| 6,296,630 B1 | 10/2001 | Altman | |
| 6,298,272 B1 | 10/2001 | Peterfeso et al. | |
| RE37,463 E | 12/2001 | Altman | |
| 6,346,099 B1 | 2/2002 | Altman | |
| 6,358,247 B1 | 3/2002 | Altman et al. | |
| 6,363,286 B1 | 3/2002 | Zhu et al. | |
| 6,405,091 B1 * | 6/2002 | Vachon et al. | 607/120 |
| 6,416,510 B1 | 7/2002 | Altman et al. | |
| 6,501,994 B1 | 12/2002 | Janke et al. | |
| 6,506,408 B1 | 1/2003 | Palasis | |
| 6,546,292 B1 * | 4/2003 | Steinhaus et al. | 607/116 |
| 6,547,787 B1 | 4/2003 | Altman et al. | |
| 6,671,562 B2 | 12/2003 | Osypka et al. | |
| 6,879,861 B2 * | 4/2005 | Benz et al. | 607/116 |
| 6,985,777 B2 * | 1/2006 | Tsuboi et al. | 607/132 |
| 7,187,980 B2 * | 3/2007 | Osypka et al. | 607/120 |
| 2002/0077685 A1 | 6/2002 | Sundquist et al. | |
| 2002/0138123 A1 * | 9/2002 | Casas-Bejar et al. | 607/120 |
| 2003/0083646 A1 * | 5/2003 | Sirhan et al. | 604/891.1 |
| 2003/0104028 A1 * | 6/2003 | Hossainy et al. | 424/424 |
| 2005/0070985 A1 | 3/2005 | Knapp et al. | |

FOREIGN PATENT DOCUMENTS

| | | |
|---|---|---|
| EP | 0791372 A1 | 8/1997 |
| JP | 5-192414 | 8/1993 |
| JP | 9-225042 | 9/1997 |
| JP | 2002-528235 | 11/1999 |
| JP | 2002-528235 | 9/2002 |
| JP | 04-597133 | 12/2010 |

OTHER PUBLICATIONS

International Search Report and Written Opinion issued in PCT/US2004/032064, mailed Dec. 21, 2004.

* cited by examiner

DRUG-ELUTING ELECTRODE

TECHNICAL FIELD

The present invention relates generally to leads for conducting electrical signals to and from the heart. More particularly, it pertains to electrodes for leads.

BACKGROUND

Leads implanted in the body for electrical cardioversion or pacing of the heart are generally known in the art. In particular, electrically transmissive leads may be implanted in or about the heart to reverse (i.e., defibrillate or cardiovert) certain life threatening arrhythmias or to stimulate contraction (pacing) of the heart. Electrical energy is applied to the heart via one or more electrodes on the leads to return the heart to normal rhythm. Leads have also been used to sense conditions, materials or events (generally referred to as "sense" or "sensing") in the body, such as in the atrium or ventricle of the heart and to deliver pacing pulses to the atrium or ventricle. Tachy leads generally can at least sense, pace, and deliver defibrillation shocks. Brady leads can at least perform the combination functions of pacing and sensing the heart. One of the available functions of the pacemaker or the automatic implantable cardioverter defibrillator (AICD) is to receive signals from a lead and interpret signals. In response to these signals, the pacemaker can pace or not pace. The AICD can pace or not pace, and shock or not shock.

Some leads include drug eluting structures proximate the electrodes to deliver therapeutic drugs near the electrode/tissue interface. However, current leads utilize either a drug plug or a drug collar to store and control the release of the drugs. However, as leads become smaller, the size of the drug plugs and collars becomes incompatible with the lead size. Moreover, a higher impedance electrode design is desirable, since it increases the battery life of the implantable device.

SUMMARY OF THE INVENTION

In one aspect a lead includes a lead body and an electrical conductor. An electrode is coupled to the electrical conductor. The electrode includes a coating on at least a portion of a surface of the electrode, the coating including two or more layers, with a first layer adjacent the surface of the electrode comprising an insulative material and a second layer adjacent the first layer comprising at least one pharmacological agent.

DETAILED DESCRIPTION

In the following detailed description, reference is made to the accompanying drawings which form a part hereof, and in which is shown by way of illustration specific embodiments in which specific aspects of the broader invention may be practiced. These embodiments are described in sufficient detail to enable those skilled in the art to practice both the broad concepts of the invention as well as more limiting specific constructions, and it is to be understood that other embodiments may be utilized and that structural changes may be made without departing from the spirit and scope of the present invention as disclosed herein. Therefore, the following detailed description is not to be taken in a limiting sense, and the scope of the present invention is defined by the appended claims.

Figure 1:
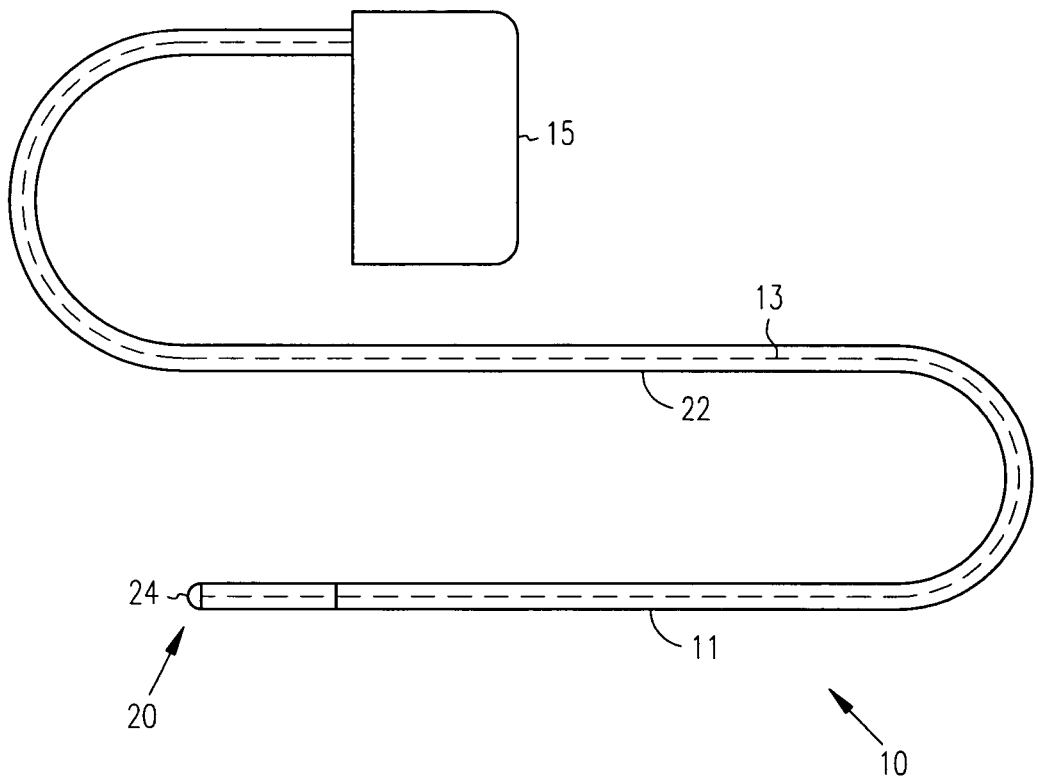
FIG. 1 shows a lead and pulse generator in accordance with one embodiment.

FIG. 1 shows a lead 10 coupled to a pulse generator 15. Lead 10 comprises a lead body 11, an elongate conductor 13 contained within the lead body, and a lead tip 20 with an electrode 24 at the lead tip 20. A brady lead body is shown, although some embodiments of the present system can be incorporated with other leads, such as tachy leads. The lead body 11 consists of electrical conductors 13 which are covered by a biocompatible insulating material 22. Polymers, such as silicone rubber, fluorinated resins, polyacrylates, polyamides ceramic or composite materials or other insulating material can be used for covering the lead body 11.

Figure 2:
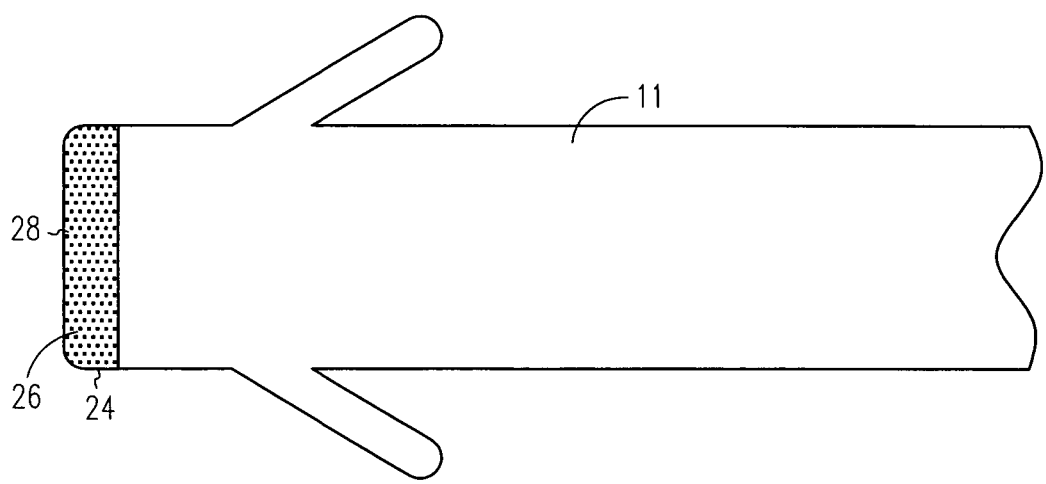
FIG. 2 shows an electrode in accordance with one embodiment.

FIG. 2 shows a side view of electrode 24, in according with one embodiment. Electrode 24 includes a base material body 26 which can include titanium, platinum, and platinum iridium, among other material. A coating 28 covers at least a portion of the outer surface of the electrode. As will be detailed below, coating 28 includes one or more pharmaceutical agents to provide therapy to the tissue adjacent the electrode when the electrode is implanted. Electrode 24 is designed to be in contact with endocardium or myocardium tissue and to deliver both pacing therapy and therapeutic agents to the site of trauma. The therapeutic agents, either a homogeneous drug or a combination of several drugs, are fixated to the surface of the electrode.

Applying coating 28 directly to the electrode allows for the removal of a drug collar from the lead. This saves significant space on the tip configuration. Additionally, by placing the therapeutic agent directly on the electrode surface, there is an immediate proximity to the site of trauma. The therapeutic agent will be more efficient at reaching the wound. While a single drug agent can be utilized, a combination of drugs having various properties (anti-inflammatory and anti-proliferative for example) allow for more thorough treatment of affected cell types.

Figure 3:
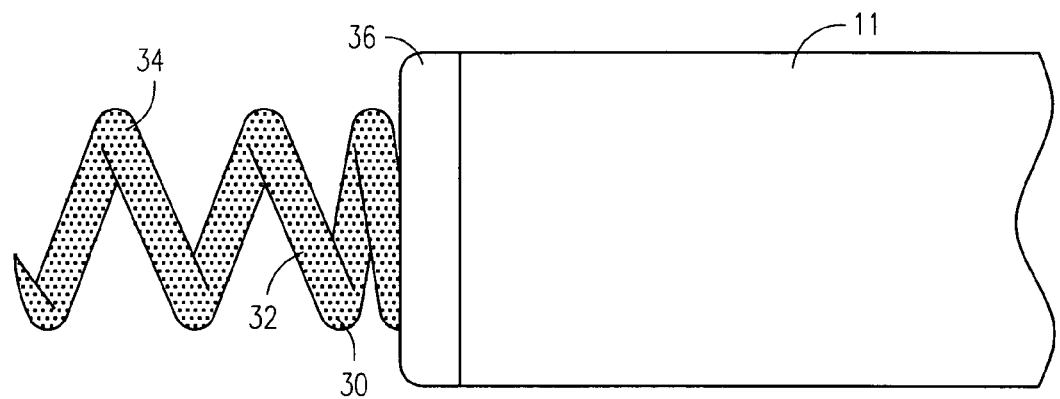
FIG. 3 shows a helix in accordance with one embodiment.

FIG. 3 shows a helix 30 coupled to lead 11, in accordance with one embodiment. Helix 30 includes a body 32 having a coating 34 covering at least a portion of the helix surface. Coating 34 is similar to coating 28 described above, and the above discussion is incorporated herein. Helix 30 provides a technique for securing an electrode assembly to the heart. In one embodiment helix 30 can be coupled to conductor 13 (FIG. 1) and can be formed of an electrically conductive material offering low electrical resistance and is also resistant to corrosion by body fluids. A biocompatible metal, such as titanium, platinum, or platinum-iridium alloy are examples of suitable materials. Alternatively, the helix 30 can be electrically inactive or insulated. In one embodiment, helix 30 can be constructed of a rigid, corrosion resistant, non-electrically-conductive material (e.g., a ceramic). For example, helix 30 can extend through a mesh electrode 36 at the distal end of lead 11. In some embodiments, helix 30 can be retractable, as known in the art.

Figure 4:
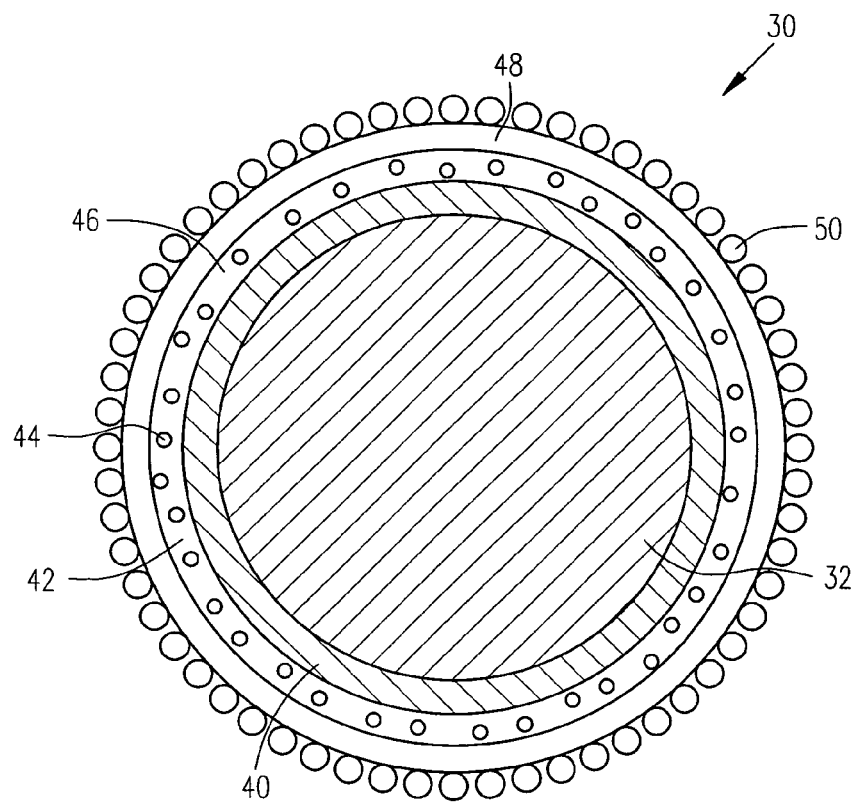
FIG. 4 shows a cross section view of the helix of FIG. 3.

FIG. 4 shows a cross section of coating 34 of helix 30 of FIG. 3. Coating 34 is similar to coating 28 and the following discussion applies to coating 28 of electrode 24 also. The drug-coated electrode 30 is used for delivering therapeutic agents to the site of contact with the endocardium. The layers of coating 34 are not shown to scale in FIG. 4, but are shown thicker for sake of clarity.

In one embodiment, coating 28 includes from the surface of helix body 32 outward: a first layer 40, such as a polymer primer layer that also functions to increase electrode impedance, a second layer 42 comprising a therapeutic layer which can include a pharmacological agent 44 and polymer matrix 46, a third layer 48 including a release-control layer of polymer, and a fourth layer 50 including a layer of pure drug. Characteristics of the coatings such as surface area of coverage, layer thickness, and mass ratio can be varied. In some embodiments, one or more of the layers described above can be omitted.

In one example, first layer 40 can include a polymeric base coat on the electrode surface. The polymeric base coat can include an ethylene vinyl alcohol. The material used for the coating is biocompatible and, in one option, non-thrombogenic. In other embodiments, materials such as Parylene™, polyurethanes, polyacrylates (including polymethacrylates), polyesters, polyamides, polyethers, polysiloxanes, polyepoxide resins and the like can be used. Typically, the coating of first layer 40 is at least one micron up to about 100 microns in thickness. In some embodiments, the coating is between 1 and 30 microns, between 1.5 and 20 microns, between 1.5 and 15 microns, or between 2 and 10 microns.

First layer 40 acts as a primer layer for attaching second layer 42 and also provides increased impedance by insulating at least a portion of the electrode surface. In one embodiment, the insulated portion can cover a majority of the electrically active surface of the fixation helix, leaving a relatively small uninsulated region of the fixation helix. This approach functionally increases the impedance of the electrode to reduce energy dissipation in pulsing functions, such as pacing functions. Other varying embodiments include, but are not limited to, a portion which is approximately or substantially equal to half of the fixation helix, and a portion which is approximately or substantially equal to a minority of the fixation helix. Such embodiments provide different amounts of uninsulated region and different amounts of impedance.

In one embodiment, second layer 42 includes a polymer and drug matrix to deliver and gradually release a therapeutic or pharmacological agent 44 intended to prevent the formation of scar tissue around the electrode. The pharmacological agent may consist of either one drug or a combination of drugs depending on the desired affect. Providing several different drugs to the area of trauma will allow for more complete treatment of cellular responses to the electrode. For example, second layer 42 can comprise a matrix comprising a polymer 46, such as one of the polymers discussed above for layer 40, and at least one pharmacological agent 44, wherein the second layer at least partially covers the polymeric base coat 40.

The pharmacological agent 44 can include an anti-arrhythmic agent, an angiogenic growth factor, an anti-inflammatory agent, an anti-proliferative agent, an anti-coagulant, an antibiotic, or a combination thereof. In one embodiment, the agent 44 agent is dexamethasone, clobetasol, beclomethasone, paclitaxel, actinomycin-D, everolimus, or a pharmaceutically acceptable salt thereof.

The ratio of pharmacological agent to polymer in the second layers can be 30% to 40% by weight in some embodiments. Other embodiments have a ratio of up to 44% by weight, up to 50% by weight, and up to 60% by weight. Some embodiments can be less than 30% or greater than 60%.

In one embodiment, third layer 48 includes a porous barrier including a polymeric coating having a porosity to regulate the release of the pharmacological agent 44 from the matrix. In various examples, the polymers discussed above can be used for third layer 48. In one embodiment, the third layer has a thickness of about 1 or 2 microns. In some embodiments, the third layer 48 is coated multiple times to provide the desired porosity.

In one example, the outer, fourth layer 50, a drug-only coat, functions to provide immediate therapeutic treatment to the site of electrode contact and tissue trauma. Single or multiple drug configurations may be used in the fourth coating layer 50.

In one embodiment, the fourth coating layer 50, composed strictly of drug, will be exposed to tissue upon implant and will provide immediate therapy to the site of trauma while the second layer 42 will be responsible for a more regulated, chronic release of drug therapy. This combination of both quick and chronic release will better prevent the formation of scar tissue. This in turn will lower acute and chronic voltage thresholds.

In one embodiment, fourth layer 50 can include an anti-arrhythmic agent, an angiogenic growth factor, an anti-inflammatory agent, an anti-proliferative agent, an anti-coagulant, an antibiotic, or a combination thereof. The pharmaceutical agent of the fourth layer can include dexamethasone, clobetasol, beclomethasone, paclitaxel, actinomycin-D, everolimus, or a pharmaceutically acceptable salt thereof.

One technique to form the electrode described above is coating or spraying the tip with a first layer of a polymeric base coat and then coating the helical tip with a second layer, wherein the second layer comprises a polymer and at least one pharmacological agent, and at least partially coats the first layer. In other examples, the coatings of any of the layers can be applied by any convenient method, including, but not limited to coating (e.g., dip coating), printing, spraying, brush application, resist application and removal and the like.

It is to be understood that the above description is intended to be illustrative, and not restrictive. Although the use of the lead has been described for use in a cardiac pacing system, the lead could as well be applied to other types of body stimulating systems. Many other embodiments will be apparent to those of skill in the art upon reviewing the above description. The scope of the invention should, therefore, be determined with reference to the appended claims, along with the full scope of equivalents to which such claims are entitled.

What is claimed is:

1. An apparatus comprising:
an electrical lead comprising a lead body and an electrical conductor; and
an electrode coupled to the electrical conductor, wherein the electrode includes a coating disposed on at least a portion of a surface of the electrode, the coating including three or more layers, with a first layer comprising an insulative polymeric base material adjacent to and in contact with at least a portion of the surface of the electrode for insulating at least a portion of the electrode and increasing an impedance of the electrode, a second layer disposed over and in contact with at least a portion of the first layer, the second layer including an insulative polymer matrix material and a first pharmacological agent, and a third layer disposed over the second layer, wherein the third layer consists of a drug.

2. The apparatus of claim 1, wherein the electrode includes a helical tip.

3. The apparatus of claim 1, wherein the first pharmacological agent comprises an anti-arrhythmic agent, an angiogenic growth factor, an anti-inflammatory agent, an antiproliferative agent, or a combination thereof.

4. The apparatus of claim 3, wherein the anti-inflammatory agent is dexamethasone, clobetasol, beclomethasone, or a pharmaceutically acceptable salt thereof.

5. The apparatus of claim 1, wherein the drug is any one of an anti-arrhythmic agent, an angiogenic growth factor, an anti-inflammatory agent or an antiproliferative agent.

6. The apparatus of claim 5, wherein the anti-inflammatory agent is dexamethasone, clobetasol, beclomethasone, or a pharmaceutically acceptable salt thereof.

7. The apparatus of claim 1, wherein the polymeric base coat is ethylene vinyl alcohol.

8. The apparatus of claim 1, further comprising a fourth layer disposed over and in contact with the second layer, wherein the fourth layer includes a porous polymeric barrier having a porosity sufficient to regulate a release of the first pharmacological agent from the second layer.

9. The apparatus of claim 1, wherein the first layer is between 1 and 100 microns thick.

10. The apparatus of claim 9, wherein the amount of the at least one pharmacological agent present in the second layer is up to 60% by weight of the second layer.

11. The apparatus according to claim 1, wherein the insulative polymeric base material is selected from the group consisting of Parylene, polyurethanes, polyacrylates, polymethacrylates, polyamides, polyethers, polysiloxanes, and polyepoxy resins.

12. A system comprising:
an electrical pulse generator;
an electrical lead releasably coupled to electrical pulse generator, wherein the electrical lead includes a lead body and an electrical conductor; and
an electrode coupled to the electrical conductor, wherein an outer surface of the electrode comprises a coating disposed on a portion of an outer surface of the electrode such that the outer surface of the electrode comprises a coated region and an uncoated region, the coating including three or more discrete layers comprising a first layer including an insulative polymeric base material adjacent to and in contact with the outer surface of the electrode such that an impedance of the electrode is increased, a second layer disposed over and in contact with the first layer, the second layer including an insulative polymer matrix material and a first pharmacological agent, and a third layer disposed over the second layer, wherein the third layer consists of a drug.

13. The system of claim 12, wherein the electrode includes a helical tip.

14. The system of claim 12, wherein the first pharmacological agent comprises an antiarrhythmic agent, an angiogenic growth factor, an anti-inflammatory agent, an antiproliferative agent, or a combination thereof.

15. The system of claim 14, wherein the anti-inflammatory agent is dexamethasone, clobetasol, beclomethasone, or a pharmaceutically acceptable salt thereof.

16. The system of claim 14, wherein the anti-inflammatory agent is dexamethasone.

17. The system of claim 12, wherein the drug is any one of an anti-arrhythmic agent, an angiogenic growth factor, an anti-inflammatory agent or an anti-proliferative agent.

18. The system of claim 17, wherein the anti-inflammatory agent is dexamethasone, clobetasol, beclomethasone, or a pharmaceutically acceptable salt thereof.

19. The system of claim 12, wherein the polymeric base coat is ethylene vinyl alcohol.

20. The system of claim 12, further comprising a fourth layer disposed between the second layer and the third layer in contact with the second layer, wherein the fourth layer comprises a porous polymeric barrier having a porosity sufficient to regulate a release of the first pharmacological agent from the second layer.

21. The system of claim 12, wherein the first layer is between 1 and 100 microns thick.

22. The system of claim 21, wherein the amount of the first pharmacological agent present in the second layer is up to 60% by weight of the second layer.

23. An apparatus comprising:
an electrical lead comprising a lead body and an electrical conductor; and
an electrode coupled to the electrical conductor, wherein the electrode includes a coating disposed on a portion of a surface of the electrode, the coating including three or more layers, with an inner layer including a first pharmacological agent dispersed within an insulative polymer matrix for increasing an impedance of the electrode and regulated, chronic release of the first pharmacological agent, an outer layer consisting of a drug such that the drug of the outer layer is exposed to tissue upon implant of the electrode, and a middle layer disposed between the inner layer and the outer layer, wherein the middle layer includes a porous polymer barrier and is adjacent to and in contact with the inner layer and not adjacent to the surface of the electrode.

24. The apparatus of claim 23, wherein the electrode includes a helix.

25. The apparatus of claim 23, further including a fourth layer directly adjacent a surface of the electrode comprising a polymer primer layer, with the inner layer adjacent the polymer primer layer.

26. The apparatus of claim 23, wherein the first pharmaceutical agent in the polymer matrix includes an anti-inflammatory drug.

27. The apparatus of claim 23, wherein the first pharmacological agent in the polymer matrix includes an anti-proliferative drug.

28. The apparatus of claim 23, wherein the amount of the first pharmacological agent present in the inner layer is up to 60% by weight of the inner layer.

29. A method comprising:
coating a portion of a surface of an electrode with a first layer, wherein the first layer comprises an insulative polymeric base coat for insulating a portion of the electrode and increasing impedance of the electrode;
coating the first layer of the electrode with a second layer, wherein the second layer comprises an insulative polymer and at least a first pharmacological agent, and at least partially coats the first layer and not the surface of the electrode; and
coating the second layer with a third layer, wherein the third layer consists of a drug.

30. The method of claim 29, wherein the drug is any one of an anti-arrhythmic agent, an angiogenic growth factor, an anti-inflammatory agent or an antiproliferative agent.

31. The method of claim 30, wherein the anti-inflammatory agent is dexamethasone, clobetasol, beclomethasone, or a pharmaceutically acceptable salt thereof.

32. The method of claim 29, wherein the polymeric base coat is ethylene vinyl alcohol.

33. The method of claim 29, further comprising a fourth layer positioned between the second and third layer, wherein the fourth layer comprises a porous polymeric barrier.

34. The method of claim 33, wherein the second layer comprises a matrix including a polymer and at least one pharmacological agent and the fourth layer regulates the release of the pharmacological agent from the matrix.

35. The method of claim 29, further comprising the step of contacting an exterior surface of the electrode with a composition comprising the insulative polymer and the first pharmacological agent to form the second layer.

36. The method of claim 35, wherein the contacting includes spraying.

37. The method of claim 29, wherein the first layer is between 1 and 100 microns thick.

38. The method of claim 37, wherein the amount of the first pharmacological agent present in the second layer is up to 60% by weight of the second layer.

* * * * *